US00PP13951P29

(12) United States Plant Patent
Doty

(10) Patent No.: US PP13,951 P2
(45) Date of Patent: Jul. 8, 2003

(54) CHERRY TREE NAMED 'DOTY'

(76) Inventor: Robin Doty, 361 O'Kelley La., Wapato, WA (US) 98951

( * ) Notice: Subject to any disclaimer, the term of this patent is extended or adjusted under 35 U.S.C. 154(b) by 0 days.

(21) Appl. No.: 09/905,739

(22) Filed: Jul. 13, 2001

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—Anne Marie Grünberg
(74) *Attorney, Agent, or Firm*—Christensen O'Connor Johnson Kindness PLLC

(57) ABSTRACT

A new and distinct variety of sweet cherry, *Prunus avium L.,* denominated 'Doty', which is similar to Rainier (not patented) but which matures 7 to 10 days earlier and has other differences in flower and fruit characteristics as described herein.

3 Drawing Sheets

LATIN NAME OF THE GENUS AND SPECIES CLAIMED

*Prunus avium L.*

VARIETY DENOMINATION

'Doty'

FIELD OF THE INVENTION

The invention relates to a new and distinct variety of cherry tree, *Prunus avium L.,* which originated as a whole tree mutation of Rainier cherry tree (not patented).

BACKGROUND OF THE INVENTION—DISCOVERY AND ASEXUAL REPRODUCTION OF THE TREE

The distinct and new variety of cherry tree originated as a whole tree mutation in an orchard of Bing and Rainier cherry trees at the farm of Robin Doty in Mattawa, Wash. In about 1990, Robin Doty noted that fruit of the single tree, still in existence, matured 7 to 10 days earlier than surrounding Rainier cherry trees in the cultivated block. In addition to the earlier maturity, the fruit from this tree showed other distinct characteristics, including a more heart-shaped appearance, milder flavor, and a semi-freestone pit, not the usual characteristics for fruit of Rainier trees. Asexual reproduction of the tree was accomplished by grafting on Mazzard seedling rootstock, and the new characteristics have been shown to be stable for more than five years at the Robin Doty orchard. No commercial propagation nor distribution has been carried out.

BRIEF SUMMARY OF THE INVENTION

The new variety has been compared to Rainier, the standard white-fleshed cherry grown in the area. Interest in this new variety arises from a generally higher demand and price for an earlier Rainier type white-fleshed cherry. At present, there is no early ripening white-fleshed cherry, and the export potential for such a cherry is substantial.

In addition to the earlier ripening, as shown by the data below, the new variety also has a shorter fruit stem (pedicel), fewer flowers per flower bud, fewer buds per spur, and a shorter filament length than Rainier. The seeds of the new variety are longer and flatter than the seeds of Rainier, and the new variety has a semi-freestone pit.

BRIEF DESCRIPTION OF THE DRAWINGS

The accompanying photographs show the following characteristics of this new variety:

FIG. 1 shows the original tree of the new variety in bloom, photographed on Apr. 10, 2000, at Mattawa, Wash.

FIG. 2 shows a close-up of flowers of the new variety (left) as compared to Rainier (right), illustrating differences in petal width and arrangement, photographed on Apr. 10, 2000, at Mattawa, Wash.

DETAILED BOTANICAL DESCRIPTION

Figure 3:
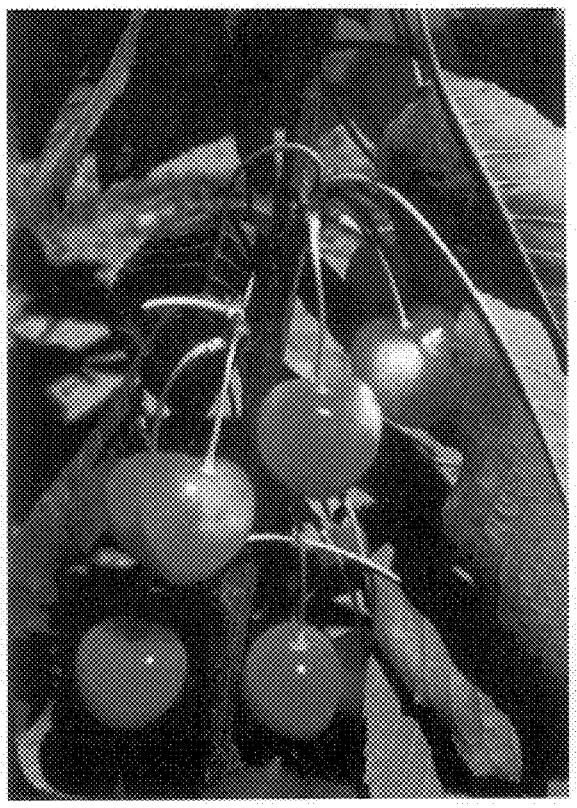
FIG. 3 shows a close-up of cherries of the new variety on the tree, photographed on Jun. 22, 1999, at Mattawa, Wash., illustrating the distinctive shape of the new variety.
Figure 4:
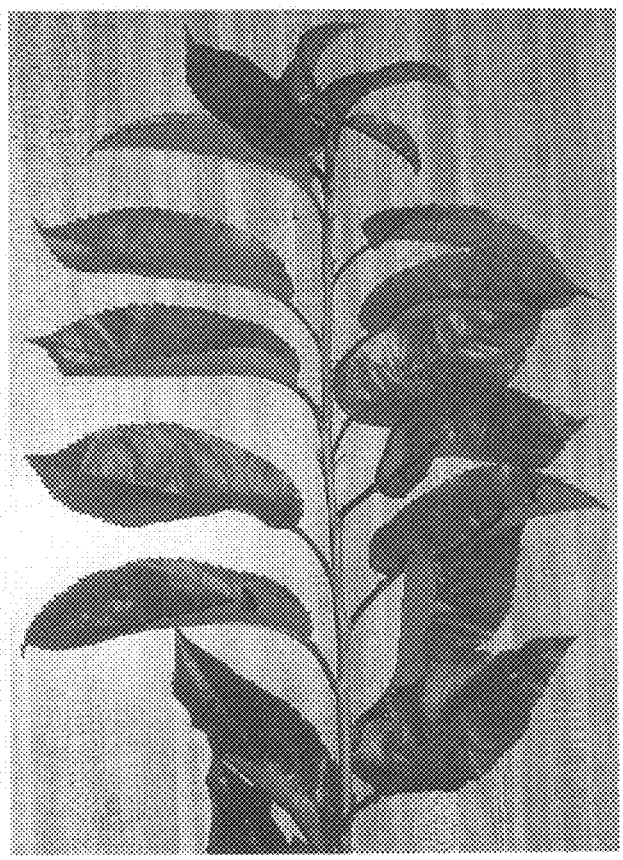
FIG. 4 shows a vegetative shoot of the new variety, illustrating leaf arrangement, stipules, and glands, photographed on Jun. 12, 2000, at Mattawa, Wash.
Figure 5:
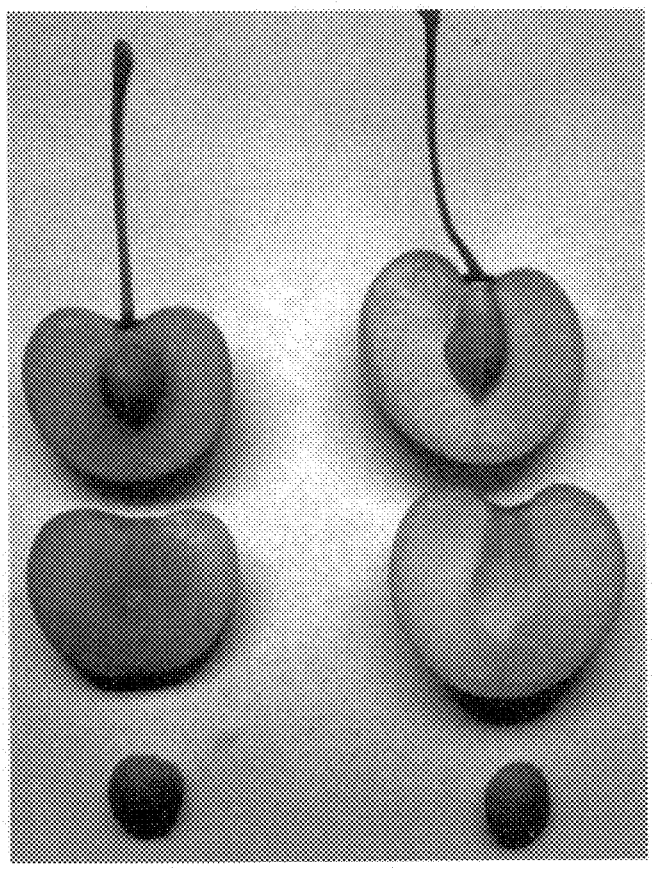
FIG. 5 shows a cross-section of a cherry of the new variety (right) as compared to Rainier (left) showing particularly the distinctive shape of the new variety, the elongated pit, and the freestone nature of the pit, photographed on Jun. 12, 2000.
Figure 6:
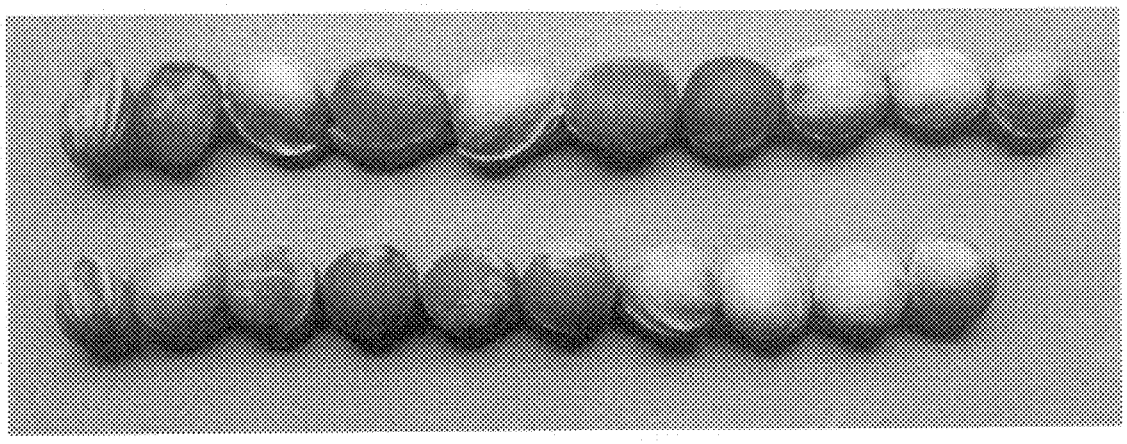
FIG. 6 shows a row of pits (seeds) of the new variety (upper row) as compared to pits (seeds) of Rainier (lower row), illustrating that the new variety has longer, flatter pits (seeds).

The following detailed description of the characteristics of the new variety of cherry tree is based on observations during the 1999 and 2000 seasons. Color terminology is in accordance with the Munsell Book of Color, Macbeth Division, Kollmorgen Instruments Corp., 405 Little Britain Road, New Winsor, N.Y., 12553.

Tree:

*Size.*—Large (6 m in height×4 m in width at 18 years of age); moderately vigorous; branching habit, upright, spreading.

*Density.*—Average for sweet cherry.

*Form.*—Round-headed when mature.

*Hardiness.*—Apparently hardy where tested (Columbia Basin, Wash.).

*Production.*—Moderately productive, possibly slightly less than Rainier.

*Bearing.*—Consistent, regular.

*Trunk size.*—Stocky (30 cm diameter at 1 m. from ground, 18 years of age).

*Trunk bark texture.*—Typical for sweet cherry.

*Trunk bark color.*—Grey-brown, 7.5 YR 3/4.

*Trunk lenticels.*—Numerous, medium, 2.0×6.0 mm in diameter, light brown (10R 8/2).

Branches:

*Branch size.*—Stocky.

*Branch texture.*—Average, typical for sweet cherry.

*Branch color.*—First year wood greenish yellow, 5 Y 5/6; second year wood brown, 10 YR 3/4.

*Branch lenticels.*—Medium density, small (0.5 mm in diameter), light tan (7.5R 8/2), Leaves: Measurements are from mature leaves attached at mid-point of actively growing, upright shoots of the year 2000 growth.

*Size.*—Leaf blade (not including petiole) medium, 12–15 cm long, 6–7 cm wide.

*Form.*—Lanceolate, with acuminate tip.

*Color.*—Upper surface glossy green, 5 GY 3/6; lower surface light green, 5 GY 3/4.

*Mid-vein.*—Medium, 2 mm thick at base, dull green, 5 GY 5/6, becoming light green toward top.

*Petiole.*—2.5–3.5 cm long, 3 mm thick at base, dark purplish red (5R 3/6) along petiole groove, mostly greenish (2.5 GY 5/4) along lower surface.

*Leaf texture.*—Smooth.

*Margin.*—Crenate to finely serrate.

*Glands.*—Mostly 2 in number, positioned alternate, reniform in shape, shiny with reddish center (7.5 R 2/8), glabrous, positioned on rim of petiole groove about 3 cm from base of leaf petiole.

*Stipules.*—Small, usually 2, 0.8–1.3 cm in length, light green (5 GY 7/2).

Flower buds: Hardy, medium size, plump, conic, average 2 per node; color, reddish-brown (2.5R 3/4).

Flowers: Self-sterile.

*First bloom.*—April 1 to 3 at Mattawa, Wash. (2-year average), the same date as Rainier.

*Size.*—Large, 35–40 mm in diameter when fully open.

*Color.*—White.

*Bloom count.*—Slightly fewer (2.9) than 3 per bud, compared with Rainier (3.5).

*Petals.*—Average length 17.3 mm, width 13.5 mm, distinctly narrower than Rainier (15.3 mm), cupped slightly inward, white.

*Anthers.*—Large, yellow (5 Y 8.5/14); 1–1.5 mm in length, similar to Rainier.

*Pollen.*—Abundant, yellow (5 Y 8.5/12).

*Filament.*—8–10 mm shorter than Rainier which is 11–12 mm; colorless.

*Pedicel.*—Short to medium length, 19–22 mm, shorter than Rainier (28–32 mm); color, pale green (2.5GY 9/2).

Fruit: Maturity when described was eating ripe (16–18 degrees Brix) Jun. 16, 2000, at Mattawa (2-year average).

*Date of first picking.*—June 5 at Mattawa.

*Date of last picking.*—June 27 at Mattawa.

*Size.*—Medium to large, 10.5 gm (10 row), diameter transversely across suture, 2.6–2.8 cm, apical diameter 2.2–2.4 cm.

*Form.*—Uniform, symmetrical, broadly cordate to occasionally oblong, rounded at apex, distinctly more heart-shaped than Rainier.

*Suture.*—Very shallow.

*Stem cavity.*—Broad, rounded shoulders, shallow.

*Base.*—Rounded.

*Apex.*—Rounded, pistil point slightly indented, indistinct.

*Stem.*—Medium thick (2 mm), variable length, 3.2 –4.5 cm, shorter than Rainier (3.5–5.0 cm), light green (5 GY 8/6).

*Skin.*—Medium thickness, rather tough (easy to peel), susceptible to cracking similar to Rainier and Bing; down: wanting; light yellow ground color (5 Y 9/4) with pinkish blush (7.5 R 8/6).

*Flesh color.*—Yellow, 2.5 Y 8.5/6.

*Flesh texture.*—Firm, crisp, similar to that of Rainier but slightly less firm, 284 g/mm for the new variety as compared to 303 g/mm for Rainier (Firmtech instrument); in spite of slightly less firmness than Rainier, the new variety does not show bruises as readily as does Rainier and hangs longer on the tree in good condition.

*Fibers.*—Few.

*Ripens.*—Moderately evenly.

*Flavor.*—Sweet, low acid, milder flavor than Rainier.

*Juice.*—Almost colorless to pale yellow (5 Y 9/4).

*Aroma.*—Very slight.

*Eating quality.*—Good.

Stone: Very shallow, semi-free, distinctly more freestone than Rainier.

*Size.*—Medium (12 mm long×10 mm wide×8 mm thick).

*Form.*—Oval, flattened, with prominent wings along basal shoulder of ventral suture, base rounded, helium small, oval, apex rounded to broadly pointed.

*Sides.*—Equal.

*Surface.*—Smooth.

*Ventral edge.*—Narrow suture subtended by 2 somewhat prominent ridges converging basically and apically.

*Dorsal edge.*—Smooth, with narrow ridge from base to apex.

*Color.*—Light yellow when dry (10 YR 8/4).

*Tendency to split.*—None.

Use: Early season shipping, fresh market.

Keeping quality: Good, at least 30 days in refrigerated storage (some stem shriveling).

Resistance to insects and diseases: Similar to other sweet cherries; no particular susceptibilities noted.

Shipping quality: Good, almost comparable to Rainier, though similarly susceptible to surface abrasion, requires careful handling.

Variance in botanical details: The cherry tree and its fruit as described herein will vary due to climate and growing conditions. The present description refers to its characteristics as grown in the Columbia Basin of Washington, near Mattawa. Comparisons are with Rainier grown at the same location and with which it is most likely to be compared. There are no other early ripening white-fleshed cherries with which to compare.

I claim:

1. A new and distinct variety of cherry tree as herein shown and described.

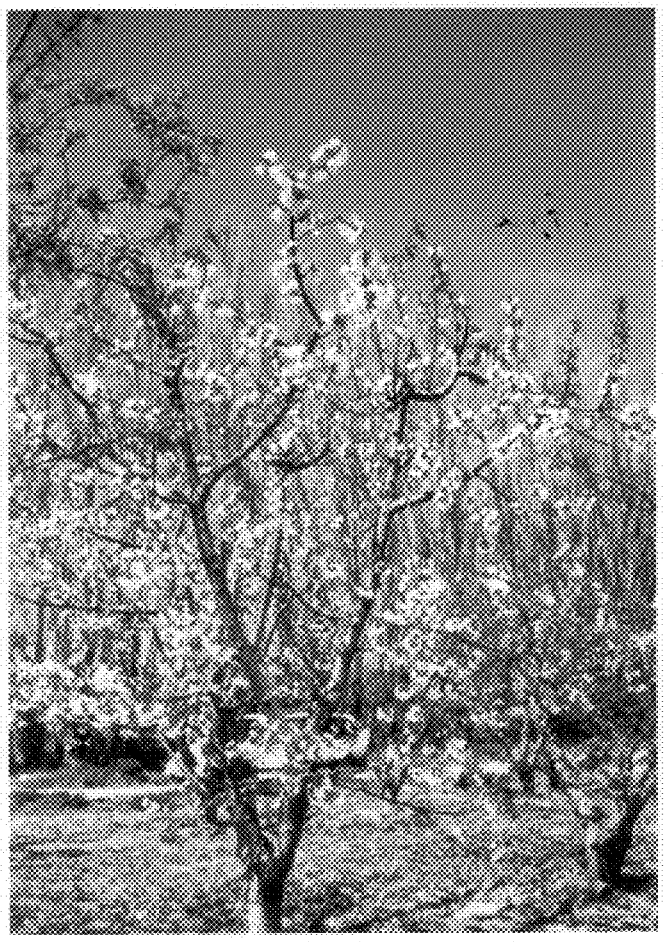
*Fig.1.*
*Fig.2.*
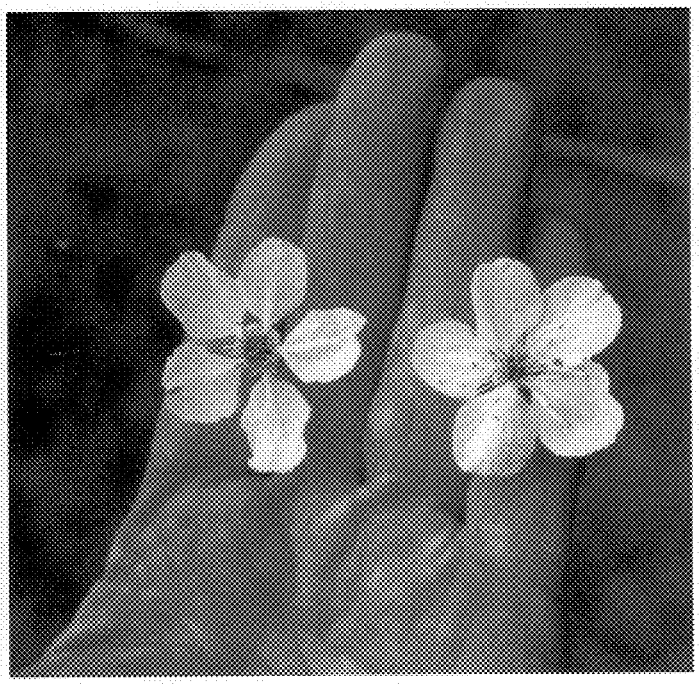

* * * * *